(12) United States Patent
Holsclaw

(10) Patent No.: US 6,802,103 B1
(45) Date of Patent: Oct. 12, 2004

(54) CLEANING TOOL

(75) Inventor: David C. Holsclaw, Warsaw, IN (US)

(73) Assignee: Nuell, Inc., Warsaw, IN (US)

( * ) Notice: Subject to any disclaimer, the term of this patent is extended or adjusted under 35 U.S.C. 154(b) by 144 days.

(21) Appl. No.: 10/263,948

(22) Filed: Oct. 3, 2002

(51) Int. Cl.[7] .............................. A46B 17/08; B23Q 3/00
(52) U.S. Cl. ............................ 15/268; 15/1; 15/257.01; 269/47
(58) Field of Search ...................... 15/1, 268, 257.01; 269/3, 6, 100, 47; 248/75

(56) References Cited

U.S. PATENT DOCUMENTS 2,365,385 A * 12/1944 Booth ......................... 451/385
5,251,356 A * 10/1993 Oaki et al. ............. 15/104.095
5,829,760 A * 11/1998 Mistrater et al. .......... 279/2.22

* cited by examiner

*Primary Examiner*—Jill Warden
*Assistant Examiner*—Laura C Cole
(74) *Attorney, Agent, or Firm*—Krieg DeVault Lundy LLP

(57) ABSTRACT

In the broader aspects of the invention, there is provided a cleaning tool for electrically and pneumatically powered surgical instruments having either a pneumatic hose connector or an electrical plug connector thereon comprising a tool body having opposite ends. An instrument connector is at one of the ends. A handle is at the other of the ends. The handle allows positive control of the positioning of the surgical instrument and positive control over both axial movement and rotary movement of the instrument during cleaning. The instrument connector of the cleaning tool provides a secure mechanical connection to the surgical instrument and a hermetic seal between the body of the tool and the body of the instrument utilizing the existing pneumatic hose or electrical plug connector structure of the instrument in a new and novel manner whereby the surgical instrument may be cleaned, scoured and disinfected without damage to the instrument or unnecessarily exposing the handle or the instrument to the cleaning and disinfectant agents utilized or the unintentional separation of the tool and the dropping of the instrument.

23 Claims, 10 Drawing Sheets

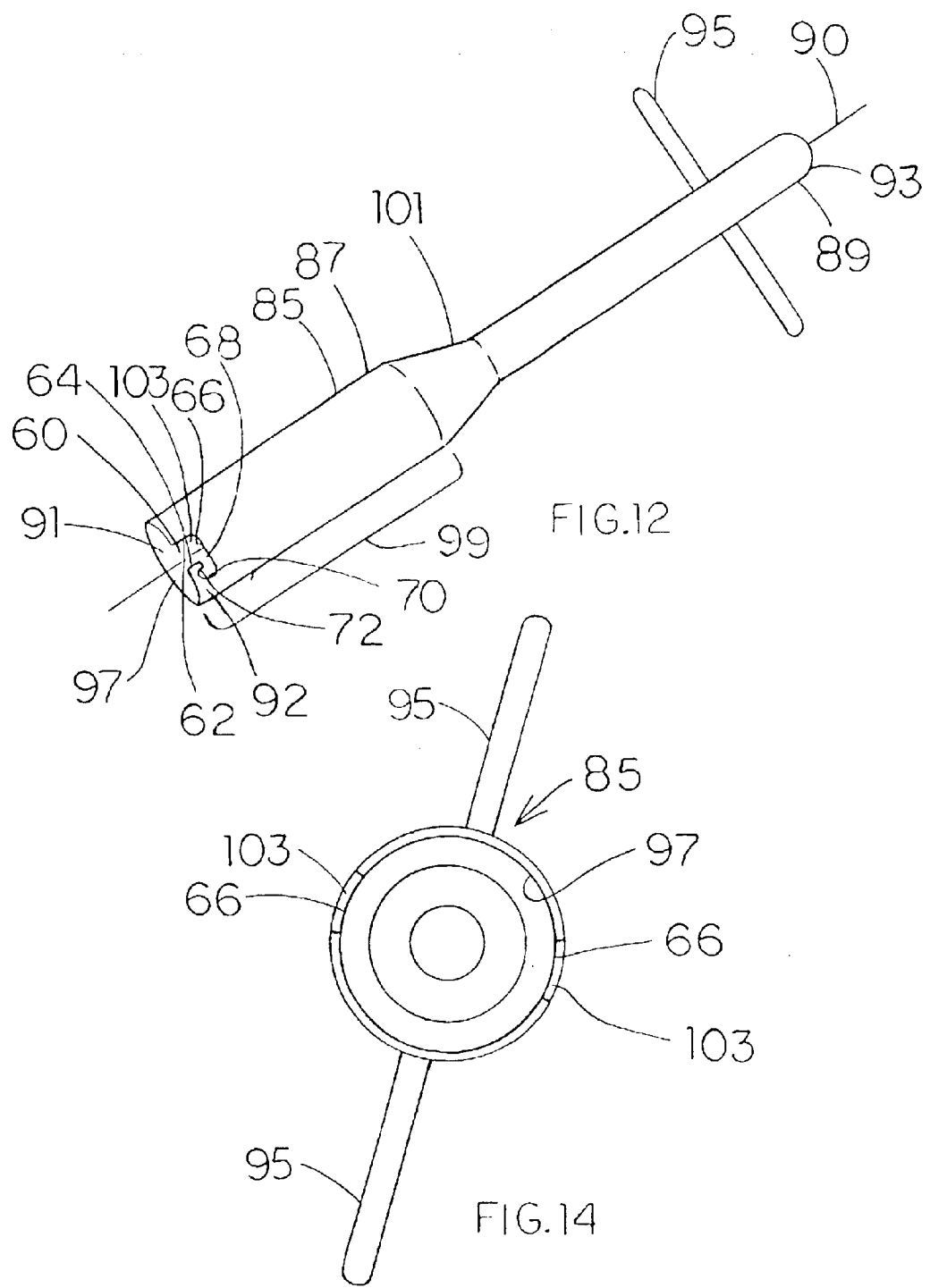

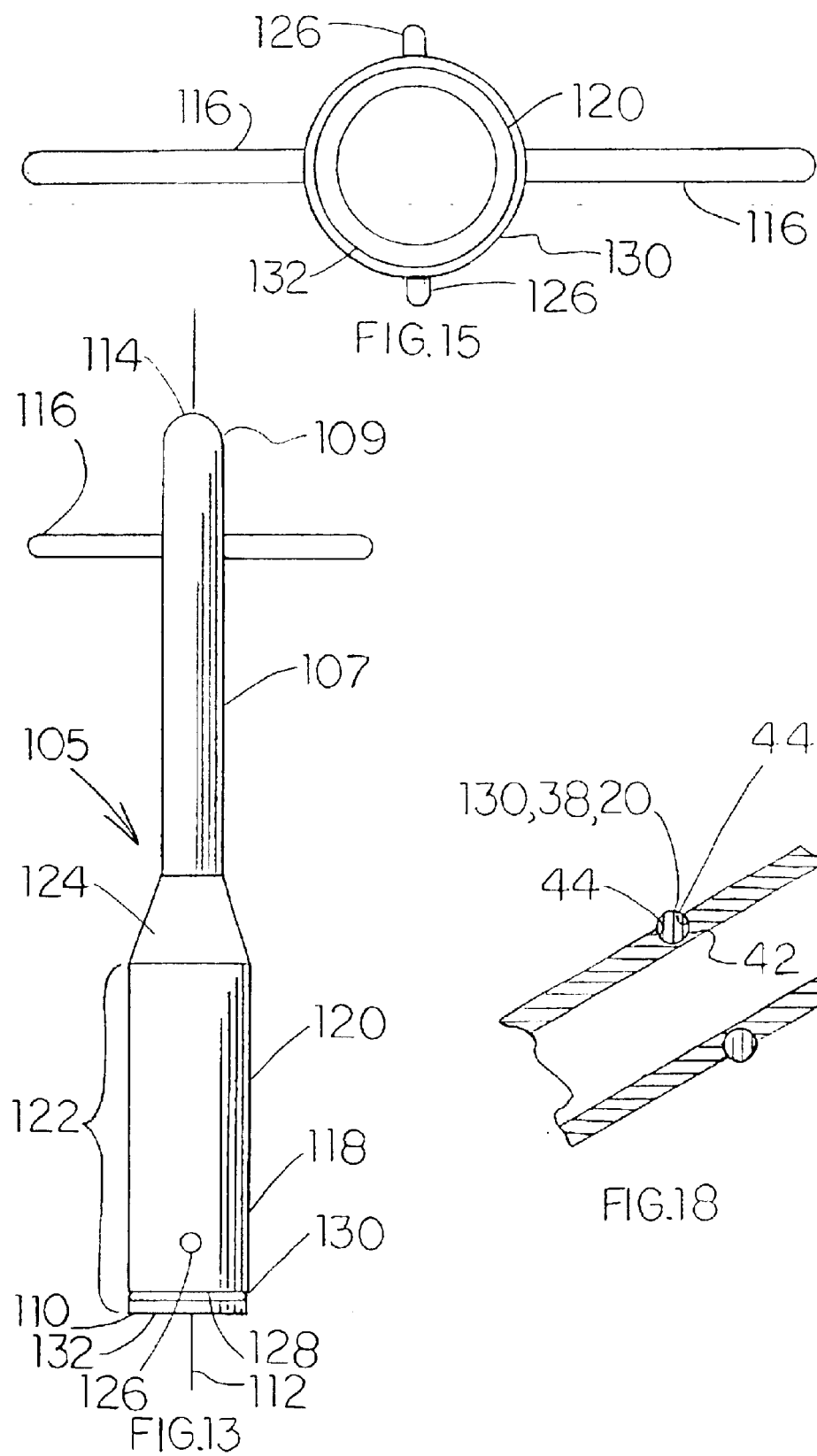

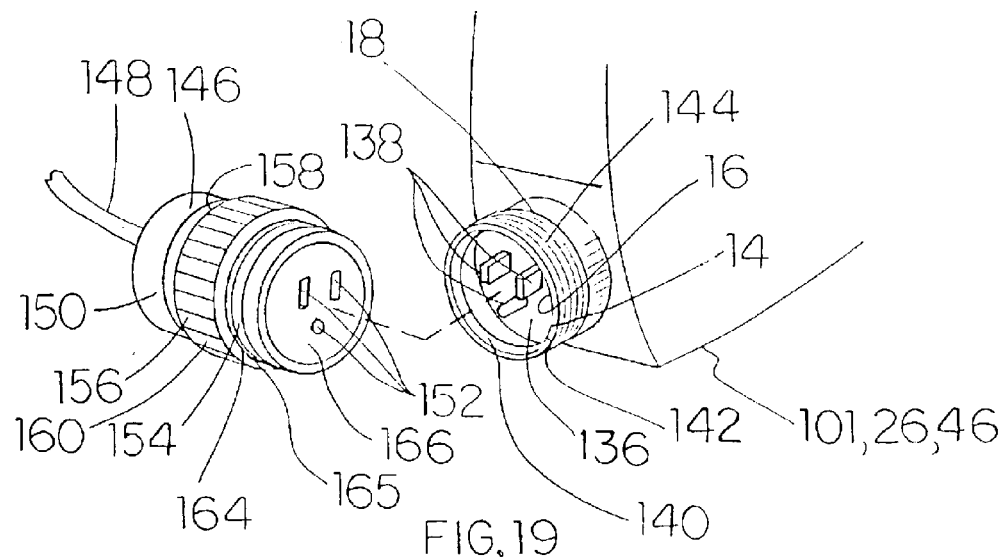
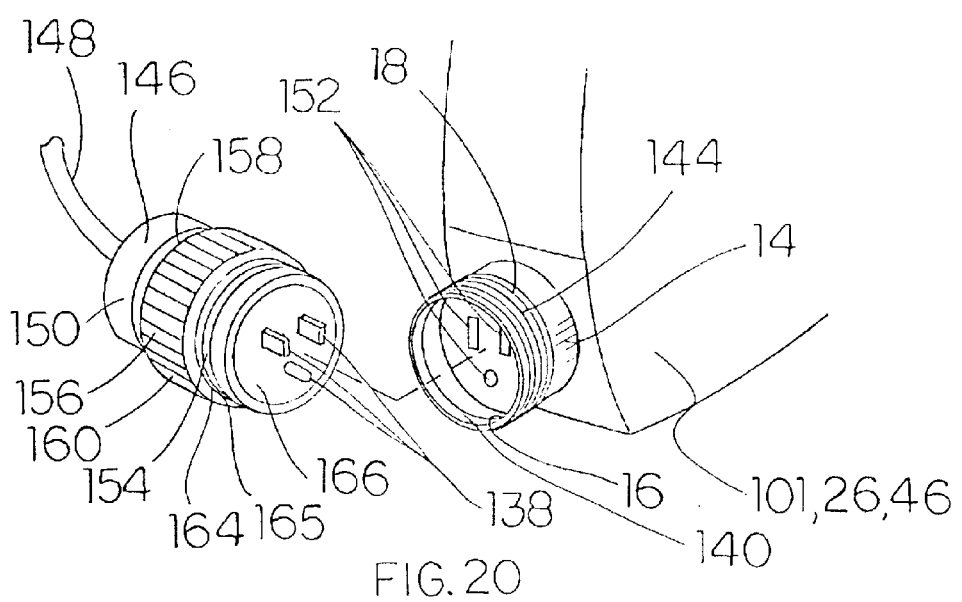

CLEANING TOOL

BACKGROUND OF THE INVENTION

The present invention relates to a cleaning tool, and more specifically to a cleaning tool for electrically and pneumatically powered surgical instruments.

Surgical instruments are, for the most part, relatively expensive, delicate, and complex devices which require cleaning and disinfecting between uses. Electrically and pneumatically powered surgical instruments in these respects are no different. However, pneumatically powered surgical instruments have moving parts and a pneumatic hose connector thereon. The pneumatic hose connector, when the instrument is in use, is connected to a connector on the distal end of an air hose (sometimes referred to as a cable) which is, at the very minimum, approximately three feet long and may extend in excess of 30 feet long, depending on the surgeon's needs or preferences. When the surgical instrument is disconnected from the hose, the pneumatic hose connector allows access to the interior of the surgical instrument and all of the moving parts and the mechanism of the instrument. Thus, these instruments are not handled very much without the hose being connected to the instrument. While this conventional practice keeps foreign matter and moisture from entering the surgical instrument and damaging the instrument or shortening its life, these instruments are very awkward and difficult to work with or moved when not being used in surgery because of the always connected hoses.

Electrically powered surgical instruments are similar. These surgical instruments have an electrical cord connector thereon. The electrical cord connector, when the instrument is in use is connected to a plug on the distal end of an electrical cord (sometimes referred to as a cable) which is at the very minimum approximately three feet long and may extend in excess of 30 feet long depending upon the surgeon needs or preferences. When the surgical instrument is disconnected from the cord, the electrical cord connector allows access to the interior of the surgical instrument and all of the moving parts and mechanism of the instrument. Thus, these instruments are also not handled very much without the electrical cord being connected to the instrument.

These surgical instruments need to be cleaned and disinfected like all other surgical instruments. They may need to be brushed or scoured, they may need to be exposed to mild detergents and distilled water and then require steam sterilization. The standard procedure is to clean and disinfect these instruments with the hoses connected. The cleaning and disinfecting of these instruments with the hoses connected is a very awkward and difficult procedure. Sometimes, the person cleaning the instrument will become frustrated enough to remove the hose or cord from the surgical instrument making the instrument in need of repair more often. It is therefore highly desirable to provide a new and improved cleaning tool for electrically and pneumatically powered surgical instruments. It is also highly desirable to provide a new and improved cleaning tool for electrically and pneumatically powered surgical instruments by which the hoses may be disconnected from the instrument, and the instrument safely handled, cleaned and disinfected without the exposure of the innards of the instrument to cleaning or disinfecting agents, moisture or other foreign matter such that the surgical instrument may be fully operational over the intended life of the instrument without the need for unexpected repair. It is also highly desirable to provide a new and improved cleaning tool for electrically and pneumatically powered surgical instruments by which the hose connector of the instrument may be hermetically sealed during handling, cleaning and disinfecting of the instrument.

The term "hermetically sealed" is used herein to refer to a sealed joint by which moisture, air, water and other contaminants are kept from migrating across the seal. The term "hermetically sealed" does not mean that the seal is "waterproof" at pressures above 20 pounds per square foot, but the "hermetically sealed" joint of the invention would prevent hot water and mild detergents from traversing the seal during the scouring, scrubbing, brushing, and rinsing operations that are generally used in cleaning surgical instruments as described herein below.

Surgical instruments of this nature are usually cleaned with hot water and mild detergents, scouring the instrument with small brushes, scrubbing the instrument, and partially directing water streams on the instrument.

Presently, the instructions for cleaning electrically and pneumatically powered surgical instruments include the steps of:

(1) removing all attachments from the main instrument;

(2) thoroughly scouring the instrument and attachments with a brush and mild detergent until all traces of blood, coagulated material, disinfectant stains, etc. are removed with the ten foot or longer hose attached to the instrument;

(3) rinsing all traces of detergent from the instrument under a running faucet with the distal end of the instrument pointed downwardly and the hose attached;

(4) do not bring the instrument in contact with any saline solution as such solutions cause corrosion of the metal and delicate moving parts, (similarly, do not use chemical disinfectants; they will damage the instrument);

(5) do not clean the instrument in ultrasonic cleaners as they will dislodge oil from the bearings causing irreversible instrument damage;

(6) never immerse the instrument, as immersion in any solution will permanently damage the instrument from liquid entering the mechanical parts corroding metal and delicate moving parts or breaking down the internal lubricants;

(7) liquid or chemical disinfectants will damage the instrument;

(8) instruments must be carefully handled and not dropped. If dropped, the instrument must be returned for service;

(9) steam sterilize the instrument (except the regulator). The instrument cannot be gas sterilized without damage.

Thus, it is highly desirable to provide a cleaning tool which can be securely connected to electrically and pneumatically powered surgical instruments in a manner which provides both a secure handle for the instrument and a liquid-tight or hermetic seal for the hose connector of the instrument. It is also highly desirable to provide a cleaning tool for electrically and pneumatically powered surgical instruments which locks onto the surgical instrument for handling, cleaning and disinfecting whereby the instrument cannot be unintentionally dislodged from the tool and dropped. It is also highly desirable to provide a new and improved cleaning tool for electrically and pneumatically powered surgical instruments that provides a positive control over the positioning of the instrument in streams of water and provides positive control over the axial movement of the surgical instrument or rotary movement of the surgical instrument in a scouring or scrubbing process without dislodging the surgical tool therefrom.

The hospital aids, nurses and others handling the surgical instruments in cleaning or disinfecting the surgical instruments, will usually be wearing rubber gloves to protect their hands from exposure to blood, tissue, hot water, steam, detergents, and other cleaning or disinfecting agents utilized in cleaning the tool. Thus, it is highly desirable to provide a new and improved cleaning tool for electrically and pneumatically powered surgical instruments having a handle that is radiused without corners or edges and is provided with a smooth surface without any projections, snags, catches or the like which could puncture, tear or otherwise destroy the integrity of a rubber glove during the use of the tool.

The new and improved cleaning tool of the invention may also need to be cleaned and sterilized. Thus, the tool is preferably made of metals or plastics known to be durable and cleanable and useable with all known disinfecting and sterilization agents. It is therefore highly desirable to provide a new and improved cleaning tool for electrically and pneumatically powered surgical instruments made of highly durable material known to be readily cleaned and disinfected and sterilized by the same agents and processes that the surgical instruments are cleaned, disinfected and sterilized. It is also highly desirable to provide a new and improved cleaning tool for electrically and pneumatically powered surgical instruments that is highly durable and resistant to damage due to dropping, compression, bending, twisting, or impact.

The person utilizing the new and improved cleaning tool of the invention will bear some risk of some exposure to disinfecting agents and sterilization agents utilized in cleaning the surgical instrument. It is therefore highly desirable to provide a new and improved cleaning tool for electrically and pneumatically powered surgical instruments having a handle which extends away from the surgical instrument a distance to allow the user of the tool to avoid exposure to the cleaning, disinfecting and sterilization agents used with the instrument.

As with all medical implements, availability, cost, and convenience in use are always factors. Therefore, it is highly desirable to provide a new and improved cleaning tool for electrically and pneumatically powered surgical instruments which is highly durable, relatively inexpensive, and simple to use.

Finally, it is highly desirable to provide a new and improved cleaning tool for electrically and pneumatically powered surgical instruments having all of the above features.

SUMMARY OF THE INVENTION

It is therefore an object of the invention to provide a new and improved cleaning tool for electrically and pneumatically powered surgical instruments.

It is also an object of the invention to provide a new and improved cleaning tool for electrically and pneumatically powered surgical instruments by which the hoses may be disconnected from the instrument, and the instrument safely handled, cleaned and disinfected without the exposure of the innards of the instrument to cleaning or disinfecting agents, moisture or other foreign matter such that the surgical instrument may be fully operational over the intended life of the instrument without the need for unexpected repair.

It is also an object of the invention to provide a new and improved cleaning tool for electrically and pneumatically powered surgical instruments by which the hose connector of the instrument may be hermetically sealed during handling, cleaning and disinfecting of the instrument.

It is also an object of the invention to provide a cleaning tool which can be securely connected to electrically and pneumatically powered surgical instruments in a manner which provides both a secure handle for the instrument and a liquid-tight or hermetic seal for the hose connector of the instrument.

It is also an object of the invention to provide a cleaning tool for electrically and pneumatically powered surgical instruments which locks onto the surgical instrument for handling, cleaning and disinfecting whereby the instrument cannot be unintentionally dislodged from the tool and dropped.

It is also an object of the invention to provide a new and improved cleaning tool for electrically and pneumatically powered surgical instruments that provides a positive control over the positioning of the instrument in streams of water and provides positive control over the axial movement of the surgical instrument or rotary movement of the surgical instrument in a scouring or scrubbing process without dislodging the surgical tool therefrom.

It is also an object of the invention to provide a new and improved cleaning tool for electrically and pneumatically powered surgical instruments having a handle that is radiused without corners or edges and is provided with a smooth surface without any projections, snags, catches or the like which could puncture, tear or otherwise destroy the integrity of a rubber glove during the use of the tool.

It is also an object of the invention to provide a new and improved cleaning tool for electrically and pneumatically powered surgical instruments made of highly durable material known to be readily cleaned and disinfected and sterilized by the same agents and processes that the surgical instruments are cleaned, disinfected and sterilized.

It is also an object of the invention to provide a new and improved cleaning tool for electrically and pneumatically powered surgical instruments that is highly durable and resistant to damage due to dropping, compression, bending, twisting, or impact.

It is also an object of the invention to provide a new and improved cleaning tool for electrically and pneumatically powered surgical instruments having a handle which extends away from the surgical instrument a distance to allow the user of the tool to avoid exposure to the cleaning, disinfecting and sterilization agents used with the instrument.

It is also an object of the invention to provide a new and improved cleaning tool for electrically and pneumatically powered surgical instruments which is highly durable, relatively inexpensive, and simple to use.

Finally, it is an object of the invention to provide a new and improved cleaning tool for electrically and pneumatically powered surgical instruments having all of the above features.

In the broader aspects of the invention, there is provided a cleaning tool for electrically and pneumatically powered surgical instruments having either a pneumatic hose connector or an electrical plug connector thereon comprising a tool body having opposite ends. An instrument connector is at one of the ends. A handle is at the other of the ends. The handle allows positive control of the positioning of the surgical instrument and positive control over both axial movement and rotary movement of the instrument during cleaning. The instrument connector of the cleaning tool provides a secure mechanical connection to the surgical instrument and a hermetic seal between the body of the tool and the body of the instrument utilizing the existing pneumatic hose or electrical plug connector structure of the instrument in a new and novel manner whereby the surgical instrument may be cleaned, scoured and disinfected without damage to the instrument or unnecessarily exposing the handle or the instrument to the cleaning and disinfectant agents utilized or the unintentional separation of the tool and the dropping of the instrument.

BRIEF DESCRIPTION OF THE DRAWINGS

The above-mentioned and other features and objects of the invention and the manner of attaining them will become more apparent and the invention itself will be better understood by reference to the following description of an embodiment of the invention taken in conjunction with the accompanying drawings wherein:

FIG. 12 is a side view of the new and improved cleaning tool for pneumatically powered surgical instruments of the invention;

FIG. 13 is a side view of a modified version of the new and improved cleaning tool for pneumatically powered surgical instruments of the invention;

FIG. 14 is an end view of the new and improved cleaning tool for pneumatically powered surgical instruments of the invention shown in FIG. 12;

FIG. 15 is an end view of the new and improved cleaning tool for pneumatically powered surgical instruments of the invention shown in FIG. 13;

FIG. 18 is a fragmentary, cross-sectional side view of the O-ring detail of the male pneumatic hose connector and the new and improved cleaning tool of the invention illustrated in FIG. 13;

FIG. 19 is a fragmentary and perspective view of a typical electrically powered surgical drill/reamer hand piece showing the electrical cord connector having a male plug therein;

FIG. 20 is a fragmentary and perspective view of a typical electrically powered surgical drill/reamer hand piece showing the electrical cord connector having a female plug therein.

DESCRIPTION OF A SPECIFIC EMBODIMENT

Figures 1, 2:
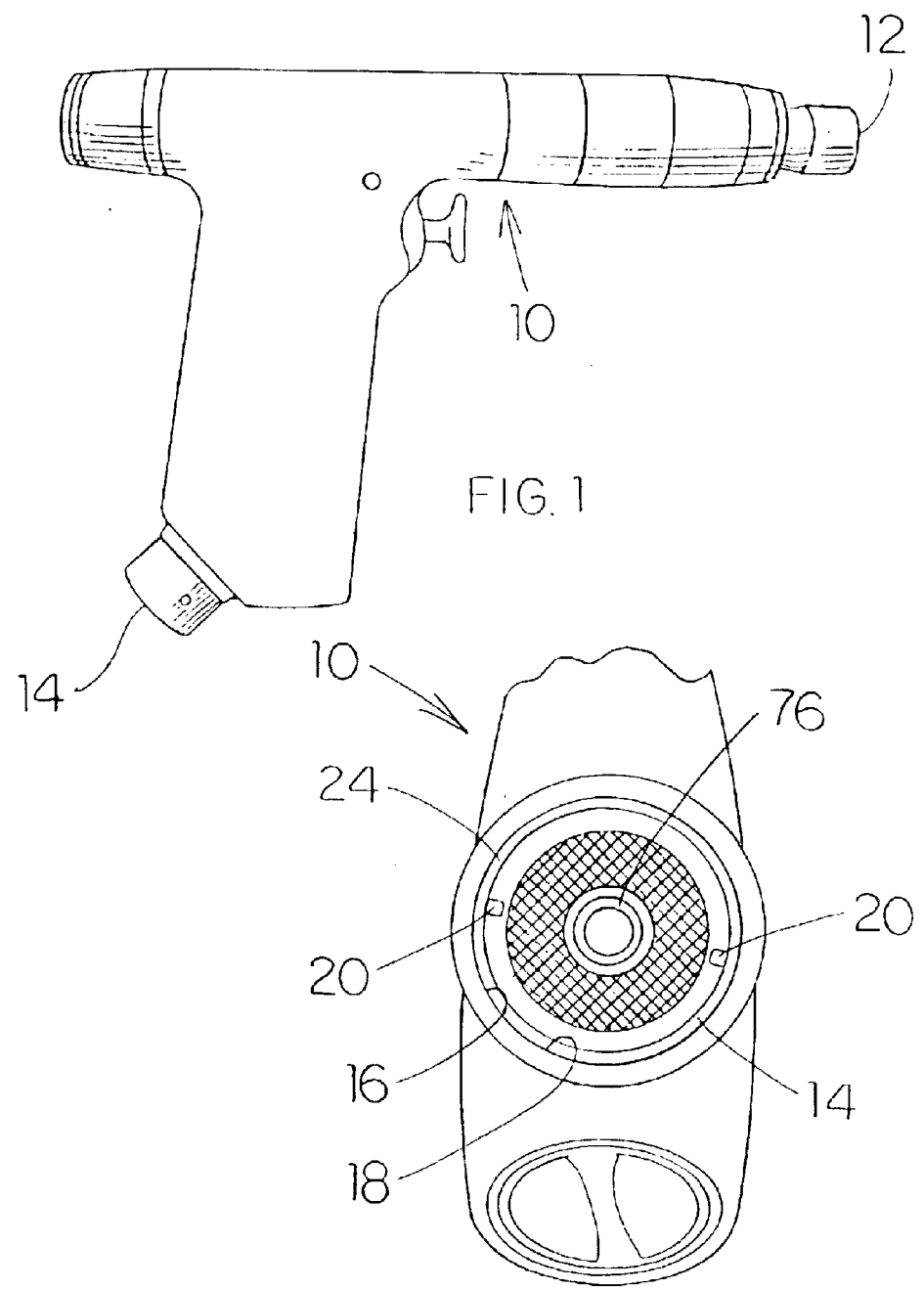
FIG. 1 is a side view of one typical air powered, surgical drill/reamer hand piece showing the pneumatic hose connector.
FIG. 2 is a fragmentary end view showing the inside of the female/male hose connector illustrated in FIG. 1.

Referring to FIGS. 1 and 2, there is shown a surgical instrument 10 having a distal end 12 and a hose end 14. Hose end 14 has a bore 16 and a cylindrical surface 18 extending coaxially thereof and a pair of opposed detents 20 for the attachment of a hose 22 and an O-ring 24 in bore 16 between the end 14 and the detents 20 to make a hermetic seal between the hose 22 and the instrument's hose end 14.

Figure 3:
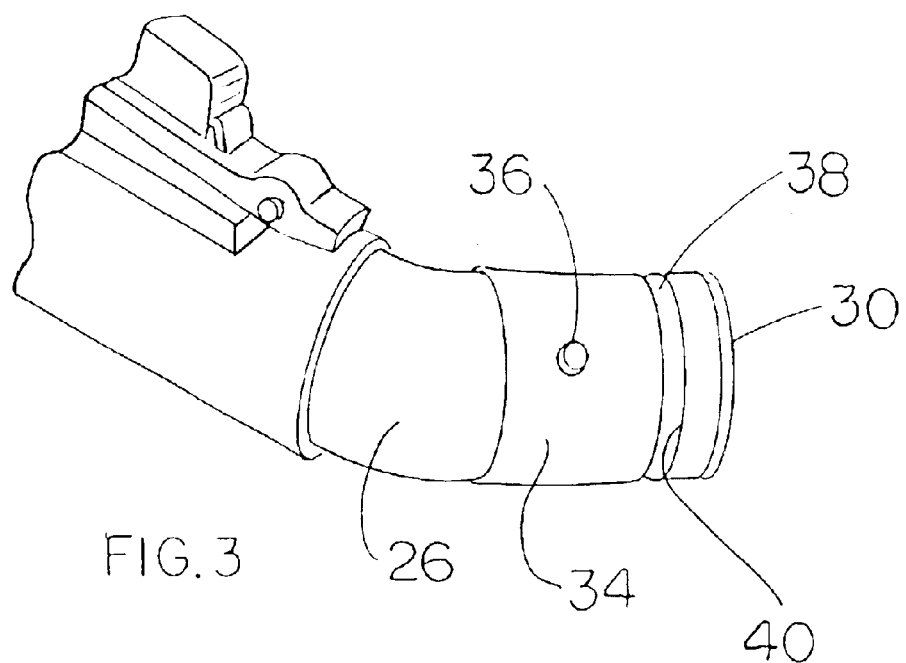
FIG. 3 is a fragmentary side view like FIG. 1 of another pneumatically powered surgical instrument showing a different pneumatic hose connector.
Figure 4:
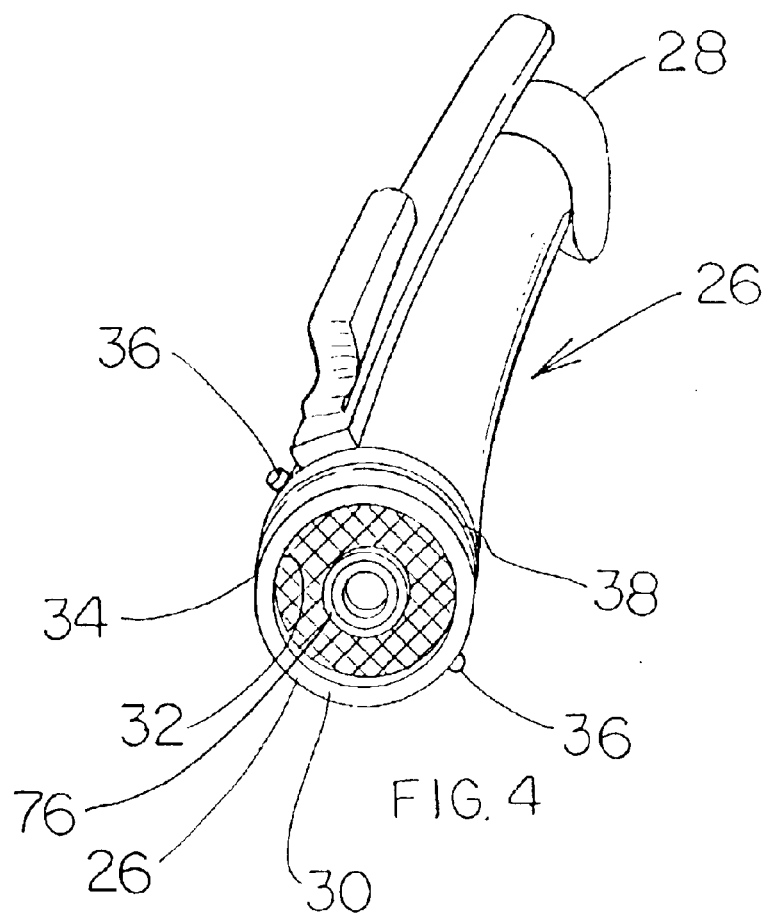
FIG. 4 is an end view of the interior of the male/male hose connector illustrated in FIG. 3.

Referring to FIGS. 3 and 4, another surgical instrument 26 is shown to have a distal end 28 and a hose end 30 is shown. Hose end 30 has a bore 32 and cylindrical surface 34 extending coaxially thereof and a pair of detents 36 extending radially outwardly therefrom for the attachment of a hose 22. An O-ring 38 is positioned between detents 36 and the hose end 30. Bore 32 is free of both detents 16 and O-ring 20.

In both versions 10, 26 of the surgical instrument O-rings 24, 38 are positioned in an O-ring slot 40 properly dimensioned to provide a hermetic seal between hose ends 14 and 30 and hose 22. Slot 40 has bottoms 42 coaxial of bores 16, 32 and cylindrical surfaces 18, 34 and two upstanding spaced apart and generally parallel side walls 44. See FIG. 18.

Figure 5:
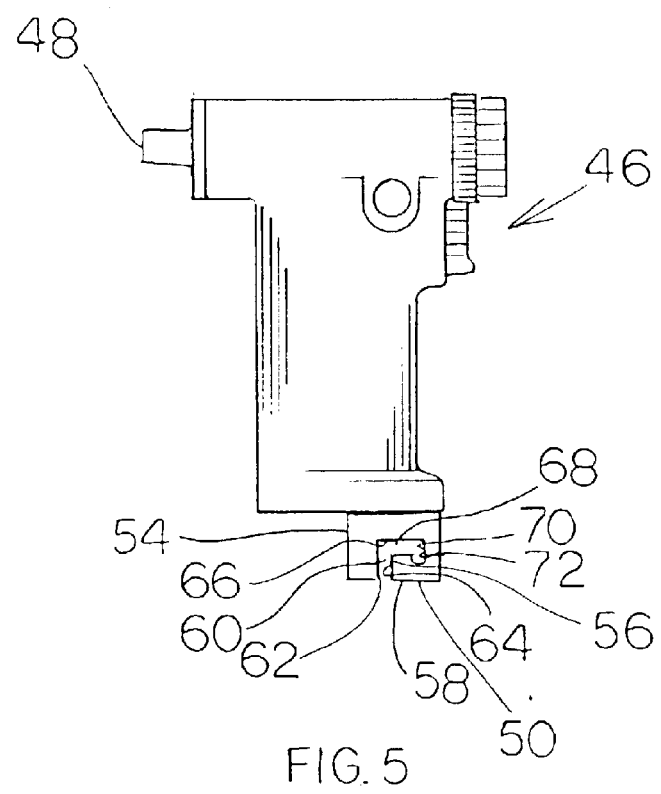
FIG. 5 is a side view of another pneumatically powered surgical instrument showing a different pneumatic hose connector.
Figure 6:
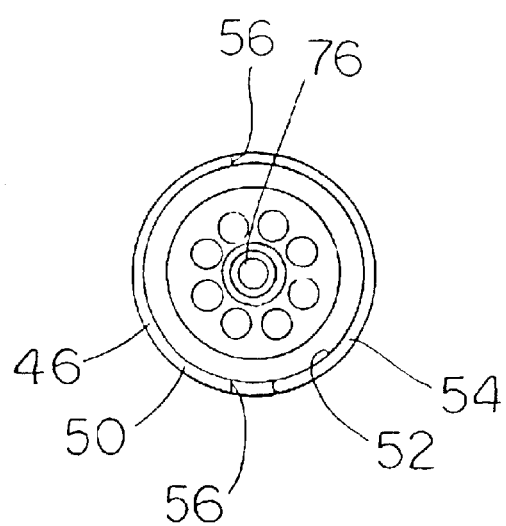
FIG. 6 is an end view showing the interior of the female/male hose connector illustrated in FIG. 5.
Figure 7:
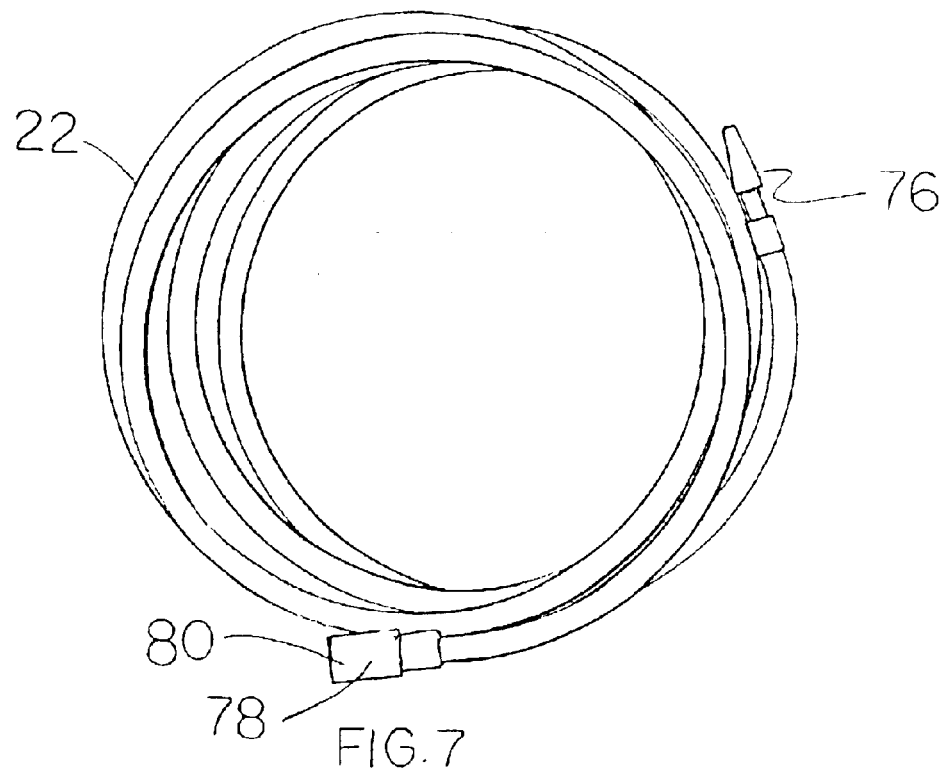
FIG. 7 is a side view of a hose with both male and female hose connectors secured to the opposite ends thereof.

Referring to FIGS. 5 and 6, there is shown still another version 46 of a pneumatically driven surgical instrument having a distal end 48 and a hose end 50. Hose end 50 is distinguished from hose end 14 and 30 above-described by its structure. Hose ends 14, 30 have detents 20, 36 and O-rings 24, 38 either within bore 16 or extending radially outwardly from cylindrical surface 34 whereas hose end 50 does not have detents 20, 36, O-rings 24, 38 or bores 16, 32 but instead, has a bore 52 coaxially extending therein. Surrounding bore 52 is a cylindrical thin wall 54. Wall 54 has extending therein an L-shaped opening 56 from its distal end 58. L-shaped opening 56 has a rectangular portion 60 which extends axially of hose end 50 from distal end 58 inwardly. Rectangular portion 60 has opposite; generally parallel sides 62, 64 and a bottom 66. Bottom 66 extends generally transversely of hose end 50 from one wall 62 past the opposite wall 64 to form the leg portion 68 of the L-shaped opening 56. Leg portion 68 includes a portion of bottom 66, an axially extending wall 70 which is generally parallel to sides 62, 64 and a hook portion 72 spaced apart and facing bottom 66. Hook portion 72 may be radiused as shown, or flat, as desired. In a specific embodiment, all corners between wall 70, sides 62, 64 and bottom 66 are radiused. In all specific embodiments, hook portion 72 is shaped to retain detents 16 in the leg portion 68 as will be further described hereinafter.

In another specific embodiment, hook portion 72 and wall 70 and the extension of bottom 66 are all radiused, forming a circular portion not shown having a portion of the circumference removed to define an opening providing communication between the rectangular portion 60 and the circular hook portion 72. The hose ends 14, 30, 50 of the surgical instruments 10, 26, 46 have significantly different structure. Some have detents 36 and O-rings 38 and O-ring slots 40 on the exterior surface 34 of hose end 30, others have detents 20 and O-rings 24 within a bore 16 of the hose end 14, still others have hose end 50 which has no O-ring 24, 38 or detents 20, 36, but instead the above-described L-shaped slot 56 and the generally cylindrical surface of bore 52.

Hose ends 14, 30, 50 may also be diverse as to size and to the structure within.

The hose ends 14, 30, 50 have coaxial male 76 hose connectors therein, respectively. The male hose connectors 76 within the hose ends 14, 30, 50 prevents any plug or stopper from being positioned therein. See FIGS. 2, 4 and 6. Hose connectors 76, 78 are conventional and found on air hoses and on other pneumatic apparatus in and around hospitals.

Figure 8:
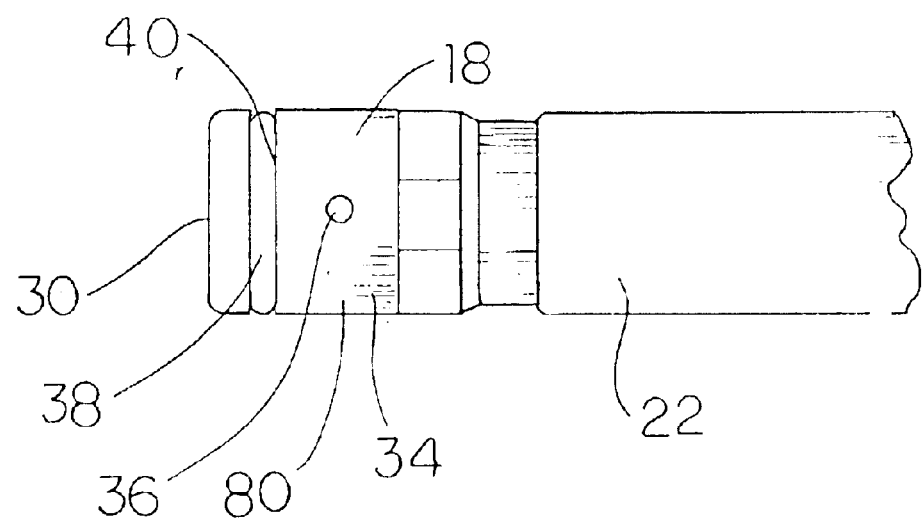
FIG. 8 is a close-up, fragmentary side view of one version of the male hose connector illustrated in FIG. 7.
Figure 9:
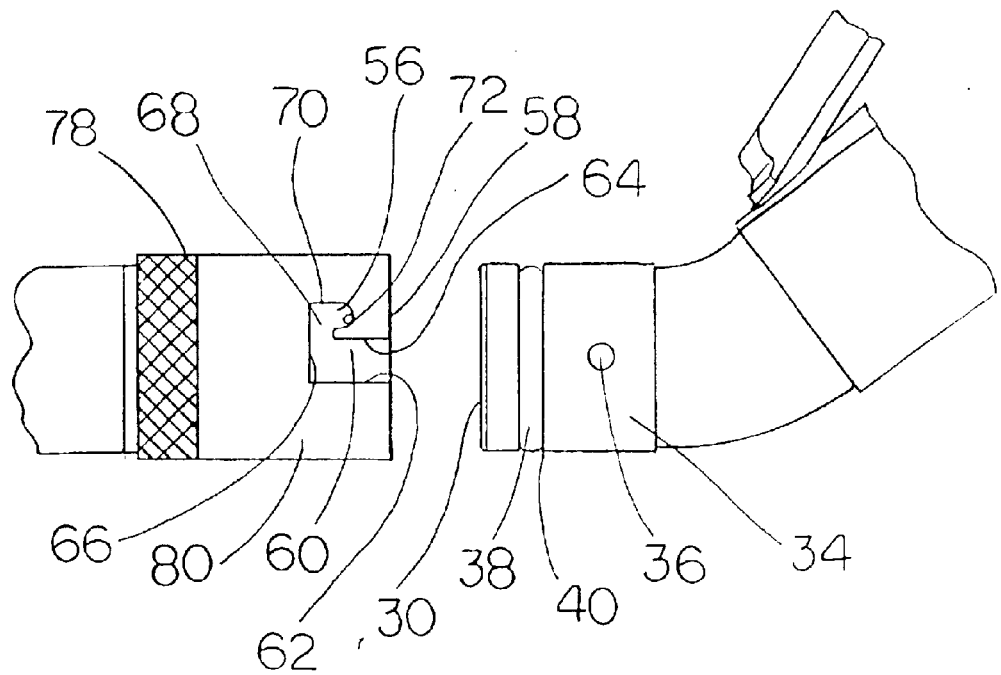
FIG. 9 is a close-up, fragmentary side view of the hose connector of the surgical instrument of FIG. 3 and of another version of the female hose connector illustrated in FIG. 7.
Figure 16:
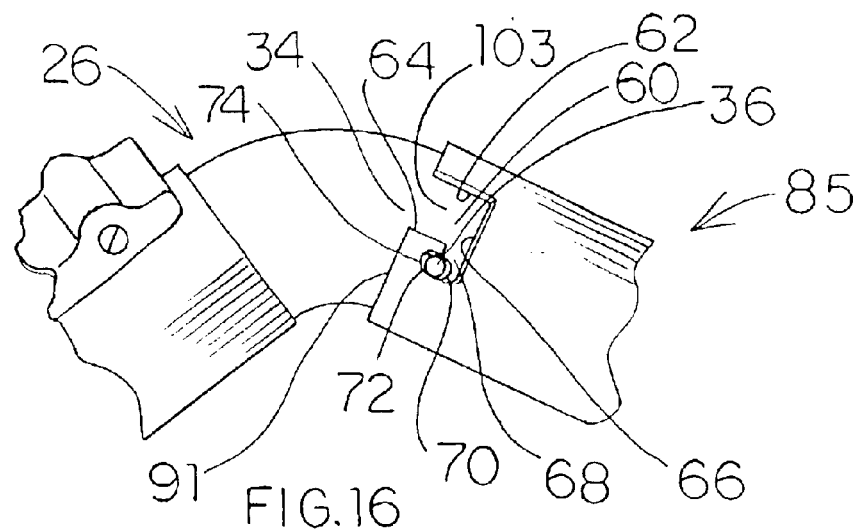
FIG. 16 is a fragmentary side view showing a pneumatically powered surgical instrument of the invention connected to the new and improved cleaning tool of FIG. 12.
Figure 17:
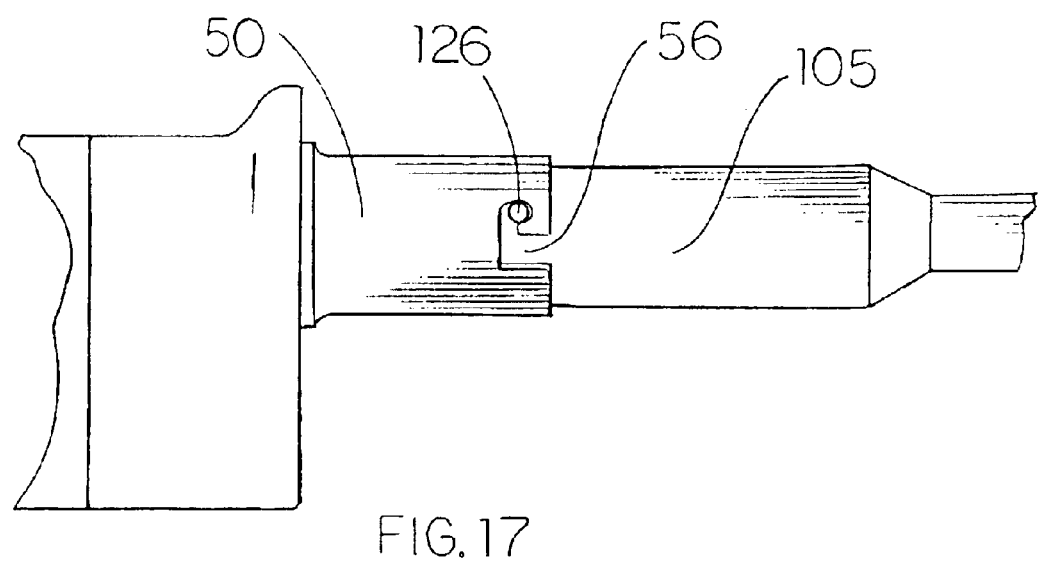
FIG. 17 is a fragmentary side view showing a pneumatically powered surgical instrument of the invention connected to the new and improved cleaning tool of FIG. 13.

Similarly, hose 22 is shown to have female 78 connectors. Hose 22 has coaxially surrounding female connector 78 a cylindrical shield 80 as shown in FIG. 9. Shield 80 is sized in some versions to slide over hose end 14 to compress an O-ring 24, 38 and engage detents 20, 36 with an L-shaped opening 56 in shield 80 (see FIGS. 9 and 16), or in other versions to slide within hose end 14 and to have an L-shaped opening 56 in shield 80 to engage detents 20, 36 and to compress O-ring 24, 38 within bore 16, 32 of hose end 14, 30, 50 (see FIGS. 2 and 17) or in yet other versions to have hose 22 to be provided a cylindrical surface with both an O-ring 24, 38 and detents 20, 36 (see FIG. 8).

In all versions of the instruments 10, 26 and 46, when connected with hose 22, the male and female connectors 76, 78 are engaged, one within the other, and the shield 80 is engaged to the hose end 14, 30, 50 by the detents 20, 36 being positioned in the L-shaped opening 56. In this position, the O-ring 24 within the O-ring slot 40 is compressed between the hose 22 and the hose end 14, 30, and 50 to form a hermetic seal therebetween. Hose connectors 76, 78 and the hermetic seal formed by O-ring 24, 36 prevents the compressed air used to drive the instruments 10, 26, 46 from leaking from the hose connection. The hermetic seal also prevents moisture and debris and other unwanted elements from immigrating into either the hose end 14, 30, 50 or within female connector 76 and male connector 78. Compressed air within the hose also tends to move connectors 76 and 78 apart. Thus, the air pressure within the hose maintains the detents 20, 36 engaged with the hook portion 72 of the L-shaped openings 56 of the connection between hose end 14, 30, 50, and detents 20, 36. The air pressure within the hose 22 thus provides a significant element of the connection between the instruments 10, 26 and 46 and the hose 22.

Both the hose 22 and the hose end 14, 30, 50 have coaxial male 76 or female 78 hose connectors thereon, respectively. The male hose connectors 76 within the hose ends 14, 30, 50 prevents any conventional plug or stopper being positioned within the hose ends 14, 30, 50 of the surgical instruments 10, 26, 46. These hose connectors 76, 78 are conventional and are found on air hoses and on other pneumatic apparatus in and around hospitals.

Figure 10:
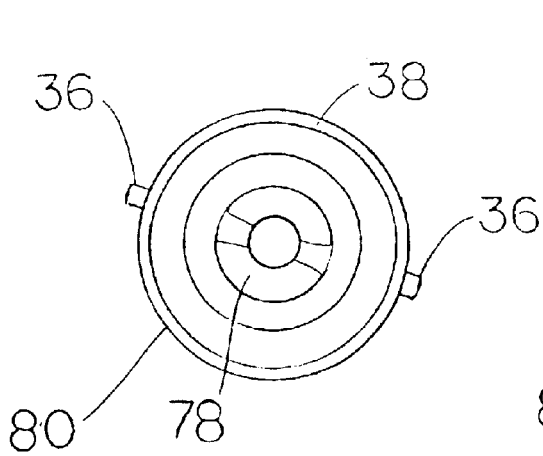
FIG. 10 is an end view of the male/female hose connector of the hand pieces shown in FIG. 8.
Figure 11:
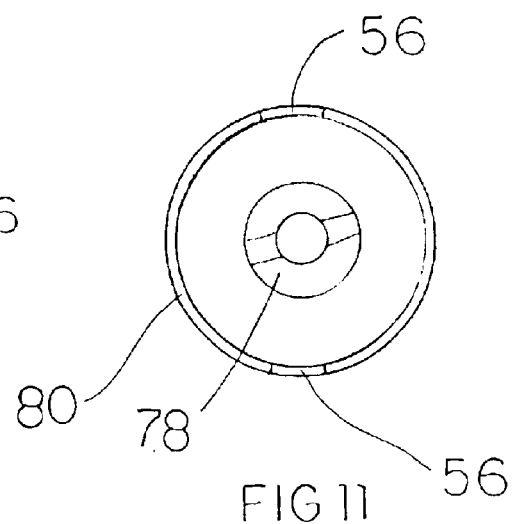
FIG. 11 is an end view of the female/female hose connector of the hand pieces shown in FIG. 9.

As shown in FIGS. 10 and 11 the hose 22 is shown to have a female connector 78 thereon. Hose 22 has coaxially surrounding the female hose connector 78 a cylindrical shield 80 as shown. The cylindrical shield 80 has a size which coaxially overlays the hose end 30 of the instrument 26 shown in FIGS. 3 and 4 and the interior surface of bore 32 compresses the O-ring 24 to make a hermetic seal between the hose 22 and the instrument 26 when properly positioned thereon. Alternatively, cylindrical shield 60 has a size which is slideably receivable into hose end 14 as shown in FIG. 2 and compresses O-ring 24 therein to make a hermetic seal between hose 22 and the instrument 10. In both instances, shield 80 has an L-shaped opening 56 extending from the distal end 28, 48, and 58 of the hose connector. L-shaped opening 56 is sized and shaped to receive the detents 20, 36 when aligned and moved longitudinally to position the shield 60 coaxially of the hose end 14, 30, 50 and then rotationally to lock the hose connector 26, 78 to the hose end 14, 30, 50 of the instrument 10, 26, 46.

When the instrument 10, 26, 46 is locked to the hose 22, the male and female hose connectors 76, 78, form a hermetic seal therebetween. Hose connectors 76, 78 prevent the compressed air driving the machine to leak from the hose connection. The hermetic seal between the hose end 14, 30, 50, and the hose connector prevents moisture, debris and other unwanted elements from immigrating into either the hose connector 76, 78 or the hose end 14, 30, 50 of the instrument 10, 26, 46.

In the cleaning operation, any migration of moisture, disinfectant or saline solution or water or steam into the hose end 14, 30, 50 will damage the instrument. Thus, the cleaning instructions from all of the major manufacturers specify that the instrument should be cleaned with the hose 22 attached, thereby relying upon the hermetic seal between the hose 22 and the hose end 14, 30, 50 of the instrument 10, 26, 46 to prevent any moisture from migrating to the mechanical parts of the instrument 10, 26, 46. Such a procedure is indeed cumbersome and unwieldy, and not convenient, as these hoses are always at least three feet long and may extend to more than 30 feet, depending upon the circumstances.

In the cleaning process, the instrument 10, 26, 46 must be handled in a secure fashion. If the instrument 10, 26, 46 is dropped, the instrument 10, 26, 46 must be sent for repair. Securance between the instrument 10, 26, 46, and any cleaning tool of the invention must be as secure as the connection between the hose 22 and the instrument 10, 26, 46.

In cleaning the instrument, the instrument 10, 26, 46 must be thoroughly scoured with a soft brush and mild detergent and scrubbed when necessary and rinsed. The instrument 10, 26, 46, often times, is shaken in drying the instrument to remove excess water from the instrument and wiped clean. Thus, any attachment of the instrument 10, 26, 46 to a cleaning tool must withstand all of this movement, scrubbing, brushing, shaking, and the like, without dropping the instrument 10, 26, 46. Any cleaning tool must be connected to the instrument in a way that not only prevents dropping the instrument 10, 26, 46, but also prevents any moisture from entering the hose end 14, 30, 50 of the instrument 10, 26, 46 during the cleaning and steam sterilization process. In all cases, at least a hermetic seal is required.

The new and improved cleaning tool demanded by the instruments 10, 26 and 46 and the recommended cleaning operation of the instruments 10, 26 and 46 is a new and improved cleaning tool 85 which can be attached to the instruments 10, 26 and 46 at the hose end 14, 30, 50 in a secure mechanical manner whereby the instruments 10, 26 and 46 can be disconnected from the hose 22 and cleaned by the recommended cleaning operation more conveniently. See FIGS. 12 and 13.

The new and improved cleaning tool 85 must provide a hermetic seal of the hose end 14, 30, 50 such that moisture, disinfectant, saline solution, water or steam will not migrate into the hose end 14, 30, and 50 and damage the instrument. Further, the mechanical connection between the tool 85 and the instruments 10, 26 and 46 must be secure during the cleaning operation such that the tool 85 will not become disengaged unintentionally from the instruments 10, 26 and 46 allowing the instruments to drop into a pan of disinfectant, saline solution, water or to drop to the floor thereby damaging the instrument.

Additionally, the cleaning tool 85 must provide a secure manner in handling the cleaning tool 85 attached to the instruments which many times will be heavier and bulkier than the cleaning tool 85 itself, in an atmosphere of moisture by a person wearing rubber gloves. Thus, while the cleaning tool 85 of the invention must have smooth surfaces without sharp edges or protrusions which may puncture the rubber gloves of the operator, the cleaning tool 85 must also not be slippery or hard to handle when wet.

Further, as the connection between the instruments 10, 26, 46 and the hose 22 by means of the hose end 14,30, 50 of the instruments and the hose connectors 76, 78 of the hose 22 rely upon the pressure of the hose to maintain the same in a locked and connected condition, it is clear that when the instruments 10, 26, 46 are disconnected from the hose 22, the air pressure within the hose will not be present to aid in the securance of any secure mechanical connection between the new and improved cleaning tool 85 of the invention and the instruments 10, 26, 46. Surprisingly, the desired secure connection which maintains the new and improved cleaning tool 85 of the invention connected to the instruments 10, 26, 46 until intentionally removed therefrom, is provided utilizing the resiliency of the O-rings 20, 24, 38 and plugs 136, 150 and similar structure as utilized in the connections at hose or cord end 14, 30, 50 of the instruments 10, 26, 46 and on the hose or cord 22 as will be described herein.

The new and improved cleaning tool of the invention allows for all surgical instruments 10 to be appropriately cleaned without necessitating the person cleaning to touch the instrument during the cleaning process. When touching is required by the cleaning process, i.e. scrubbing, brushing and the like, cleaning can occur with the instrument being fully secured by minimizing dropping instrument. After the cleaning is accomplished the instrument can be placed back in service without touching the instrument.

The new and improved cleaning tool 85 of the invention is provided with a body 87. Body 87 has opposite ends 89, 91, and an axis 90. At end 89 is an anvil surface 93. A cross bar 95 extends transversely of axis 90 through the body 87 adjacent the anvil 93. At end 91 is a connector 92. Connector 92 has a coaxial bore 97 extending inwardly of the tool 85 from end 91. Bore 97 has an axial length 99 which at all times is longer than the hose connector of end 14, 30, 50 of the instrument 10, 26, and 46. In a specific embodiment, the tool 85 adjacent end 91 is larger in size than the tool 85 adjacent end 89 thereby providing a sloped interface 101 which along with the anvil 93 provides a surface for urging the tool 85 onto the hose end 14, 30, 50 of the instrument 10, 26, 46. The user of the tool 85 will usually be wearing rubber gloves. Thus, all of the exterior surface of the tool 85 at ends 89, 91 or the breaks at the opposite ends of the interface 91 or between the body 87 and the cross bar 95 and the anvil 93 are radiused and smooth without burrs, snags, catches, or the like, which might puncture or otherwise destroy the protection of the rubber gloves.

Adjacent end 91 of the tool 85, an L-shaped slot 103 is positioned which in all functional ways is identical to the L-shaped slot 56 above-described. Slot 103 extends from end 89 inwardly such that the tool 85 at end 89 may be positioned over the hose end 30 and secured to the detents 16 of the instrument 26 in the same manner as the hose connector is secured to the instrument 26. Bore 97 of the tool 85 has a diameter which is the same as the inner diameter of the hose connector such that when the tool 85 is positioned on the instrument 26 as shown in FIGS. 3 and 4, the O-ring 24 will be compressed and a hermetic seal will be accomplished. The hermetic seal formed by the O-ring 24 will be as secure as the hermetic seal between the hose 22 and the instrument 26 during use and will maintain the securance between the tool 85 and the instrument 26.

With the instrument shown in FIGS. 1 and 2, bore 97 of the tool has a diameter which is the same as the inner diameter of the hose end 14. The tool 85 adjacent end 91 is cylindrical and thin-walled, such that when the tool 85 is positioned within end 14 of the instrument 10, the exterior surface 18 of the tool 10 will be placed in a sliding relationship with the interior surface of bore 16 of the hose end 14 of the instrument 10 to compress the O-ring 24 between and to provide a hermetic seal. This hermetic seal will be as secure as the hermetic seal between the hose 22 and the instrument 10 during use and the securance between the tool 85 and the instrument 10 will be as secure as the securance between the hose 22 and the instrument 10 during use.

A modified version 105 of the new and improved cleaning tool of the invention is provided with a body 107. See FIGS. 14 and 15. Body 107 has opposite ends 109 and 110 and an axis 112 at end 109 is an anvil 114, a cross bar 116 extends transversely of axis 112 through the body 107 adjacent anvil 114. At end 110 is a connector 118. Connecter 118 has an exterior cylindrical surface 120 extending inwardly of the tool 105 from end 110. Surface 120 has an axial length 122 which at all times is longer than the hose connector of end 14, 30, and 50 of the instruments 10, 26, 46. In a specific embodiment, tool 105 adjacent end 110 is larger in size than the tool 105 adjacent end 109 thereby providing a sloped interface 124 which along with anvil 114 provides a surface for urging the tool 105 onto hose end 14, 30, 50 of the instrument 10, 26, 46. The user of the tool 105 will usually be wearing rubber gloves thus all of the exterior surface of the tool 105 at ends 109, 110 or the breaks at the opposite ends of the interface 124 between the body 107 and the cross bar 116 and the anvil 114 are radiused and smooth without burrs, snags, catches or the like which might puncture or otherwise destroy the protection of rubber gloves.

Adjacent end 110 is a pair of detents 126. Detents 126 extend in diametric opposite directions radially outwardly of the cylindrical surface 120. Between end 110 and the detents 26 is an O-ring groove 128 in which an O-ring 130 is positioned. Extending inwardly from end 110 is a bore 132 which is coaxial to cylindrical surface 120.

In the instruments shown in FIG. 5, the surface 120 of the tool 105 has a diameter which is slightly less than the inner diameter of bore 52 of the hose end 50. The tool 105 adjacent end 110 is cylindrical and thin-walled so that when the tool 105 is positioned within end 50 of the instrument 46, the tool 105 adjacent end 110 will surround the hose connector 76, 78 and the bore 52 of the hose end 50 will compress the O-ring 130 on the tool 105 adjacent end 110 to provide a hermetic seal between the tool 105 and the instrument 50. Tool 105 adjacent end 110 will be placed in a sliding relationship with the interior surface of bore 52 and compresses the O-ring 130 therebetween. This hermetic seal will be as secure as the hermetic seal between hose 22 and the instrument 46 during use.

In all of the instruments shown in Figures, the detents 26, 36, 126 are positioned within the L-shaped opening 56, 103 of the tool 85 or the instrument 46 and the tool 85, 105 is rotated relative to the instrument 10, 26, 46 to lock the tool 85, 105 to the instrument in the same way that the hose 22 is locked to the instrument 10, 26, 46 during use. However, there is no air pressure being exerted between the instruments 10, 26, 46 and the new and improved tool 85, 105 of the invention when the instruments are connected to the hose 22; and thus, the air pressure is not that which holds the detents 16, 36, 126 within the L-shaped grooves 56, 103 and guarantees the securance between the tools 85, 103 and the instruments 10, 26, 46.

Surprisingly, the friction between the O-ring slot 40, 128 and the shield 80, and bore 16, 52, 97 are sufficient to maintain instruments 10, 26, 46 securely locked to the new and improved tool 85, 105 of the invention. When the tool 85, 105 is positioned coaxially of the hose end 14, 30, 50 of the instruments 10, 26, 46, and moved axially into coaxial position with the tool end 91, 110, in all of the versions of the instruments 10, 26, 46, the interior surface of the hose end 14, 50 or the exterior surface of the hose end 30 will be placed in a sliding relationship with the cylindrical thin-walled portion 97, 120 of the tool 85, 105 between the ends 91, 110 and the interfaces 101, 124 to compress the O-ring 24, 38, 130 within the O-ring slot 40, 128. Further axial movement in either direction causes the O-ring 24, 28, 130 to rotate within the slot 40, 128, and thus, a frictional resistance caused by the full 360 degree circumference of the O-ring 24, 38, 130 against either the bottom and side walls of the O-ring slot 40, 128 or the tool 85, 105 adjacent end 91, 110. This frictional resistance of rotation of the O-ring 24, 28, 130 is surprisingly found sufficient to prevent unintentional removal of the tool 85, 105 from the instruments 10, 26, 46 in an axial direction.

Further, the rotation of the tool 85, 105 relative to the hose end 14, 30, 50 of the instruments 10, 26, 46 slides the portion of the O-ring 24, 38, 130 protruding from the slots 40, 128 against the cylindrical surface of the tool adjacent end 91, 110 over its entire 360 degree contact with the tool 85, 105. The frictional resistance of this sliding of the O-ring in a rotary direction about the axis on which both the hose end 14, 30, 50 and the tool 85, 105 is then positioned is sufficient to prevent the detents 20, 36, 126 from becoming unintentionally rotated out of the hook portion 72 of the L-shaped slot 56, 103.

To further guarantee the securance of the tool 85, 105 to the instruments 10, 26, 46, the detents 20, 36, 126 are positioned adjacent the hook portion 72 such that both axial movement and rotational movement are required for the disengagement of the tool 85, 105 from the instruments 10, 26, 46. Surprisingly, none of the instruments 10, 26, 46 have sufficient weight to overcome this frictional resistance, either in the axial direction or in the rotary direction or about the axis upon which both the tool and the hose end 14 are positioned even when shaken or impacted, so long as the O-ring 24, 38, 130 are maintained in a good, operational condition. Thus, the O-ring should always be checked prior to cleaning the instrument and replaced if worn.

In other specific embodiments in which the hose or cord end can only be axially or longitudinally moved relative to the tool 85, 105, as when plugs 136, 150, 166 are used, spring biased detents and openings to receive the spring biased detents may be substituted for detents 20, 36 and opening 56 to accomplish the same result.

In a specific embodiment, the instruments 10 shown in FIGS. 1 and 2, have a hose connector thereon which has an exterior cylindrical surface which has a diameter of 0.985 plus 0.000 minus 0.005 inches, and an interior cylindrical surface of bore 16 that has a diameter of 0.765 plus or minus 0.003 inches, a distal end 14 which is radiused, an O-ring 24 which is positioned 0.1885 inches from the center of the O-ring to the distal end 14 of 0.848 inches plus 0.000 minus 0.005 inches, a bore 16 having an axial length of 0.655 plus or minus 0.005 inches, and a coaxially positioned male hose connector 76 which has an exterior cylindrical surface having a diameter of 0.209 inches plus or minus 0.001 inches. The instruments 10 weight approximately 2.5 pounds.

The instruments 26 have a hose end 14 which has a cylindrical surface 34 extending from the distal end 30 0.540 inches plus or minus 0.005 inches. O-ring 38 which is positioned 0.167 inches plus or minus 0.005 inches from the center of the O-ring to the distal end. The detents are positioned from the distal end 30 0.405 inches plus or minus 0.001 inches to the center of the detents. The interior diameter of the hose end 30 is 0.480 inches plus or minus 0.005 inches and the male hose connector 76 has an exterior diameter of 0.209 inches plus or minus 0.001 inches. The instruments 26 weigh approximately 5.1 ounces.

Instruments 46 as shown in FIGS. 5 and 6 have hose end 54 which has a cylindrical surface of bore 52 extending from the distal end 58 0.580 inches plus or minus 0.005 inches. O-ring 130 is positioned 0.170 inches plus or minus 0.005 inches from the center of the O-ring to the distal end 110 of tool 105. The detents 126 are positioned 0.400 inches plus or minus 0.005 inches from the center of the detents to the distal end 110. The interior diameter of the hose end bore 52 is 1.110 inches plus or minus 0.001 inches and the male hose connector 76 has an exterior diameter of 0.209 inches plus or minus 0.001 inches. The instrument weighs approximately 1.1 pounds.

In a specific embodiment, tools 85, 105 are identical in many respects. Tools 85, 105 are made of stainless steel having an axial length of approximately 6 inches. Adjacent the end 89, 109, tool 85, 105 is solid and of a cylindrical shape having a diameter of about 0.500 inches. Anvil 93, 114 is generally spherical in shape having a radius of about 0.250 inches. Cross bar 95, 116 is approximately three inches in length having distal ends which are generally spherical having a radius of about 0.125 inches. Interface 101, 124 extends from the cylindrical surface adjacent end 91, 110 to a cylindrical surface adjacent end 89, 109. Interface 101, 124 is generally conical in shape. The cylindrical surface adjacent end 89 in one embodiment is about 0.750 inches in diameter. Bore 97 is approximately 0.662 inches in diameter and extends to the interface 101. Tool 85 adjacent end 91 thus is a thin-walled tubular portion having circular cross-sections. The tubular wall of the tool 85 adjacent end 91 is approximately 0.044 inches in thickness. The cylindrical surface adjacent end 109 in one embodiment is about 0.655 inches in diameter. Bore 132 is approximately 0.434 inches in diameter and extends to the interface 124. Tool 105 adjacent end 110 thus is a thin-walled tubular portion having circular cross-sections. The tubular wall of the tool 105 adjacent end 110 is approximately 0.110 inches in thickness. The tools 85, 105 weight from about five ounces to about ten ounces.

The cylindrical surface adjacent end 89, 109 in another embodiment is about 1.100 inches in diameter. Bore 97, 132 is approximately 0.775 inches in diameter and extends to the interface 101, 124. Tool 85, 105 adjacent end 91, 110, thus is a thin-walled tubular portion having circular cross-sections. The tubular wall of the tool 85, 105 adjacent end 91, 110 is approximately 0.162 inches in thickness.

In operation, the tool 85 or the tool 105 is attached to the instrument 10, 26, 46 to be cleaned. Hose 22 is detached from the instrument 10, 26, 46 before the tool 85, 105 is attached to the instrument thereby allowing the hose to remain in the operating room and not be transported with the tool as has been required in the past and allowing the transport of the tool to the cleaning and processing area in a less cumbersome and more convenient manner. Tool 85 is either slid over or into the hose end 14, 30 of the instrument 10, 26 compressing the O-ring 24, 36, and the detents 20, 36 are slid into the L-shaped opening 103 in axial movement between the instrument 10, 26, and the tool 85. The tool 85 then is rotated relative to the instrument 10, 26 to engage the detents 20, 36 into the end of opening 103 to secure the tool 85 to the instrument 10, 26. In this manner, a secure hermetic seal is formed in the same manner as formed when the hose 22 is connected to the instrument 10, 26. Similarly tool 105 is slid into bore 52 of hose end 50 of instrument 46 compressing O-ring 130. Detents 126 are positioned in L-shaped opening 56 in the same manner to form a hermetic seal and to secure the instrument 46 to the tool 105.

When there is difficulty in securing the tool 85 or the tool 105 to the instrument 10, 26, 46 to be cleaned, the new and improved tool 85, 105 of the invention is provided with cross bar 95, 116 which allows one to put substantial pressure to move the tool relative to the instrument 10, 26, 46 axially of the tool and to rotate the tool 85, 105 once the sliding relationship between the tool 85, 105 and the instrument 10, 26, 46 is accomplished to engage the detents 20, 36, 126 in the openings 56, 103. The palm of the hand applying force to the cross bars 95, 116 and the fingers engaging the interface 101, 124 and applying additional force to the tool, the connection between the tool 85, 105 and instrument 10, 26, 46 can be accomplished.

Cross bar 95, 116 placed in the palm of the hand of the person utilizing the tool, gives that person secure handling control over both the tool 85, 105 and instrument 10, 26, 46 attached, and allows that person to accurately position the instrument where desired, and to move the instrument both axially of the tools 85, 105, and rotationally of the axis of the tools 85, 105 during the cleaning process. Because of the cross bar 95, 116, no slippage of the tool between the hand of the operator and the tools 85, 105 can occur because of the positive connection of the cross bar, even in detergent laden water.

The new and improved cleaning tool of the invention 85, 105 provides safe handling during the cleaning, disinfecting and sterilization operation of the instrument 10, 26, 46 without any chance of the exposure of the innards of the instrument 10, 26, 46 to cleaning or disinfecting or sterilization agents, moisture or other foreign matter whereby the surgical instrument 10, 26, 46 may be maintained fully operational over the intended life of the instrument.

The connection between the new and improved cleaning tool 85, 105 of the invention is as secure as the securance between the air hose 22 and the instrument 10, 26, 46 as utilized by the surgeon. As above-mentioned, the friction between the O-ring 24, 38 and the bottom and sides of the O-ring slot 40 and the O-ring 24, 38 and the cylindrical surfaces 18, 34 of bore 52 prevent the tool 85, 105 of the invention from becoming unintentionally separated from instruments 10, 26, 46 once connected.

Figure 21:
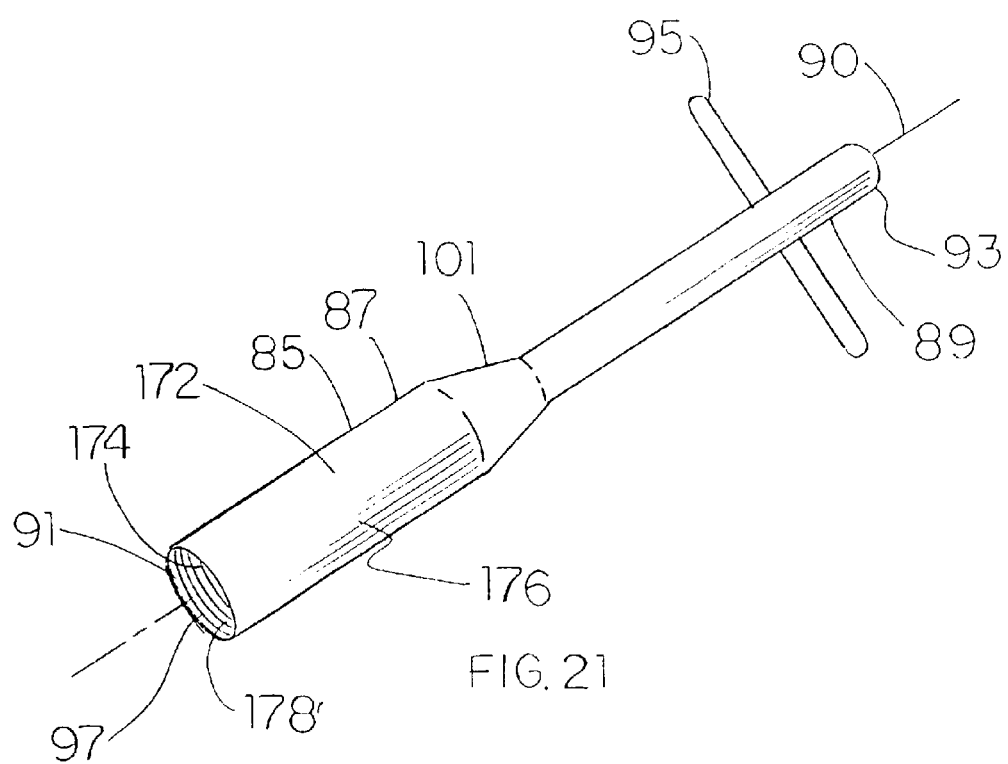
FIG. 21 is a perspective view of the new and improved cleaning tool for electrically powered surgical instruments of the invention.

Referring now to FIGS. 19, 20, and 21, there is shown an electrically powered surgical instrument 10 having a distal end 12 and a cord end 14. Electrically powered instruments 26 and 46 would have similar cord ends 14. End 14 has a bore 16 and a cylindrical surface 18 extending coaxially thereof. Within bore 16 is an electrical plug 136 of encapsulation material from which a male plug 138 extends. O-ring 140 is positioned within bore 16 between the plug 138 and the distal end of end 14. In a specific embodiment in which the corresponding female electrical plug is of resilient material, O-ring 140 may be eliminated and substituted for the resilient electrical female plug sealingly engaging the interior surface of bore 16. Cylindrical surface 18 adjacent distal end 142 is provided with threads 144 as shown.

A complimentary electrical connector 146 is attached to the electrical cord 148. Connector 146 has a female electrical plug 150 which is sized to be inserted within bore 16. Plug 150 has the conventional electrical connection slots and bore 152 therein of a female electrical connector for receiving the prongs 138 of the male connector previously described. In a specific embodiment, plug 150 is formed of resilient material which when inserted within bore 16 forms a hermetic-seal with bore 16. In another specific embodiment, the material of plug 150 is essentially rigid and non-resilient and O-ring 140 is provided within bore 16 to provide a hermetic seal between bore 16 of the instrument and the plug 150. In still another embodiment, the plug 150 is of rigid and non-resilient material and an O-ring is provided to extend from the exterior cylindrical surface of the plug 150 (not shown) to form a hermetic seal with the interior of the bore 16 upon insertion.

Spaced from the distal end of plug 150 and secured to the exterior surface of plug 150 is a ring 154. Ring 154 acts as a retainer for a cap 156 which is positioned on plug 150. Cap 156 has a bottom 158 and upstanding cylindrical sides 160 which extend over the plug 150 in a spaced apart coaxial position. Cap 156 and plug 150 thereby define a annular space therebetween. Ring 154 essentially fills this space. Bottom 158 has a coaxial opening 162 therein which is sized to permit the plug 150 to be positioned therein. Opening 162 and plug 150 and ring 154 and cap 156 are each sized to provide a sliding relationship between the cap 156 and the plug 150. Within the cap 156 adjacent the open end 164 and remote from the bottom 158, cap 156 has threads 165 positioned within the bore which are in all ways compatible with the threads 144 on the cord end 14 of the instrument. Ring 154 is spaced from the distal end of plug 150 such that when plug 150 is fully engaged with plug 136, the threads 165 are fully engaged with threads 144 and cap bottom 158 is in surface to surface contact with ring 154 thereby maintaining the plug 150 and the plug 136 in full electrical contact.

In other specific embodiments, cap 156 and cord end 14 are provided with detents 20, 36 and L-shaped openings 56 as above described which allow the cap 156 to be positioned over cord end 14, move axially and rotatably thereon to secure cap 156 and cord end 14 together as above described with plug 150 and plug 136 in full electrical contact. With these embodiments, tool 85 is fully functional therewith as above described.

Referring now to FIG. 20, there is shown a surgical instrument having a cord end 14 with a bore 16 therein and a cylindrical surface 18 thereon in which a female electrical plug 166 is positioned therein. Plug 166 has the conventional slots and holes 152 to receive the prongs 138 of a conventional male electrical plug. Connector 168 is shown for use with the plug 166 which has a plug 166 for insertion into the bore 16 with male prongs 138 of a conventional electrical connector thereon for insertion into the slots 152. Otherwise, the connector 168 is identical with the connector 146 above described. In a specific embodiment in which the plugs 150, 168 are rigid and of non-resilient material, an O-ring 140 is positioned in bore 16 between the plug 136 and the distal end of end 14 as above described. In other specific embodiments in which the O-ring is not utilized, an O-ring may be positioned on the plug 150, 168 itself adjacent to its distal end as above described or the plugs 150, 168 may themselves be of resiliently compressible material.

Referring now to FIG. 21, there is shown the new and improved cleaning tool 172 of the invention. Cleaning tool 172 is identical in all respects to the cleaning tools 85 and 105 with the exception that there are no detents 36 or L-shaped openings 56 therein. Instead, the connector 173 defines an interior bore 174 and an exterior cylindrical surface 176. Interior bore 174 has adjacent its distal end threads 178 therein which are fully compatible with the threads 144 on end 14 of the electrical power tool 134.

In operation, the tools 85, 105, and 172 function in the same manner. Only the manners by which the tools are connected to surgical instruments 10, 26, and 46 differ. Cord 148 is detached from the electrically powered instruments 10, 26, 46 before the tool 172 is attached to the instrument thereby allowing the cord to remain in the operating room and not be transported with the instrument as has been required in the past. This allows the transport of instrument to the cleaning and processing area in a less cumbersome and more convenient manner. Tool 172 is then engaged to the instrument by insertion of the plug into bore 16 and engaging the threads 162 of the cap 156 with the threads 144 of the tool end 14. By tightening the cap 156 onto the tool end 14, the cap engages the ring 154 of the plug and moves the plug into the bore 16 to ensure the connection of the prongs 138 with the slots 152 and an electrical connection therebetween. In this manner, not only a secure electrical connection is made but a secure hermetic seal is formed both when the cord 148 and the tool 172 is connected to the instruments 10, 26, and 46.

Similarly when there is difficulty in securing the tool 172 to the instruments 16, 26, 46, the new and improved tool 170 of the invention is provided with cross bar 95, 116 which allows one to put substantial pressure to secure the tool to the threads 144 of end 14 of the tool and to provide a secure hermetic seal between the new and improved tool of the invention 172 and the instrument. Cross bar 95, 116 placed in the palm of the hand of the person utilizing the tool, gives that person secure handling control over both the tool 172 and the instrument attached and allows that person to accurately position the instrument where desired and to move the instrument both axially of the tool 172 and rotationally of the axis of the tool 172 during the cleaning process. Because of the cross bar 95, 116 no slippage of the tool between the hand of the operator and the tool 172 can occur because of the positive connection of the cross bar, even in detergent laden water.

All of the new and improved cleaning tools of the invention, for example tool 85, 105, and 172 are disclosed to have a "handle" comprising an anvil 89, a cross bar 95 and a body 87 at end 89. The anvil 93, the body 87 at end 89 and the cross bar 95 can all be provided in different sizes and different shapes. However each of handles of the tools 85, 105 and 172 of the invention would have a handle having a finger grasping portion, a central locator for positioning two finger grasping portions on either side thereof and a central portion which may be pulled by the fingers comfortably into the palm of the hand to allow the person grasping the handle to have total positive control over the positioning and the axial and rotary movement of the tool during the cleaning process and to have "the feel" in both fingers and the palm confirming that control without touching the tool like the handles of the tools 85, 105 and 172.

The following terms are used herein: The term "powered surgical instrument" refers to any surgical instrument powered pneumatically or electrically or otherwise. Thus, the term "surgical instrument" includes all kinds and all shapes of instruments that are powered by some means or another. The term "power hose/cord connector" is utilized herein to refer to conventional pneumatic hoses and hose connectors, conventional electrical cords and plugs and connectors and any other conventional connector to a power hose or a power cord. The term "secure instrument connector" is utilized herein to refer to the instrument connector disclosed herein at tool end 14 where it utilizes L-shaped slots and detents, threads, spring biased detents, or other fastening devices. The term "hermetic seal" is used herein to describe a seal that is sufficiently tight to prevent steam, cleaning solutions and the like from passing the seal, but is less than a seal that would prevent water under pressure from bypassing the seal.

The term "hose end" or "cord end" is used herein to refer to that end of the instrument to which a pneumatic hose is connected, an electrical cord is connected, a battery pack is connected, and the like. The "hose end" and "cord end" are shown in the drawings to be cylindrical, but may be of any shape as determined by the manufacturer of the tool. The connectors 92, 118 and 173 of cleaning tools 85, 105 and 172 are geometrically similar to the hose end 14 of the surgical tool with which it is to be used. Similarly, the O-ring groove and the plugs 50 and 168 will be shaped as the connector 173 is shaped. Similarly, the surface 120 and the cross-section of the bore 132 will be shaped as the connector 118 is shaped, and the bore 97 will be shaped as the connector 92 is shaped.

The new and improved cleaning tool 172 of the invention like the tools 85, 105 above described provides safe handling during the cleaning, disinfecting, sterilization operation of the instrument without any chance of the exposure of the innards of the instrument to cleaning, disinfecting, sterilization agents, moisture or other foreign matter whereby the surgical instrument may be maintained in fully operation condition over the intended life of the instrument. The new and improved cleaning tool 172 of the invention covers the cord end of the instrument during handling, cleaning and disinfecting of the instrument, rendering those operations less cumbersome and more convenient. The seal between the cleaning tool 172 of the invention and the instruments 10, 26, 46 is a hermetic seal between the cord 148 and the instrument as used during surgery.

The new and improved tool 172 like the cleaning tools 85 and 105 of the invention is locked to the surgical instrument such that the instrument cannot be unintentionally dislodged from the tool and dropped. The new and improved cleaning tool 172 of the invention is provided with all of the above features.

In a specific embodiment, the new and improved cleaning tools 85, 105, 172 of the invention covers the hose end of the instrument during handling, cleaning and disinfecting of the instrument, rendering those operations less cumbersome and more convenient. The seal between the cleaning tool 85, 105 of the invention and the instrument 10, 26, 46 is a hermetic seal as secure as the hermetic seal between the hose 22 and the instrument 10, 26, 46 as used during surgery.

The new and improved cleaning tool 85, 105, 172 of the invention is locked on to the surgical instrument such that the instrument cannot be unintentionally dislodged from the tool and dropped. The new and improved cleaning tool 85, 105 of the invention is provided with all of the above features.

While the specific embodiment of the invention has been shown and described herein for purposes of illustration, the protection offered by any patent which may issue upon this application is not strictly limited to the disclosed embodiment; but rather extends to all structures and arrangements which fall fairly within the scope of the claims which are appended hereto:

What is claimed is:

1. A cleaning tool for powered surgical instruments having a conventional power hose/cord connector thereon comprising a tool body, said tool body having opposite ends and an axis extending between said ends, a secure instrument connector at one of said ends adapted to be secured to said conventional power hose cord connector, a handle at the other of said ends, said handle allowing control of said tool body over axial movement and rotary movement, said handle being spaced from said secure instrument connector, said secure instrument connector providing a hermetic seal between said tool body and said surgical instrument when secured to said surgical instrument whereby said surgical instrument may be cleaned, scoured and sterilized without damaging said instrument or unnecessarily exposing said instrument or said handle to the cleaning and sterilization agents used.

2. The cleaning tool of claim 1 wherein said secure instrument connector is adapted to be securely fastened to said power hose/cord connector of said surgical instrument, said power hose/cord connector and said secure instrument connector having sliding contiguous surfaces thereon providing said hermetic seal, and a lock, whereby said surgical instrument and said tool body may be connected and not be unintentionally disconnected once connected.

3. The cleaning tool of claim 1 wherein said secure instrument connector has the outward structure of a pneumatic hose connector.

4. The cleaning tool of claim 1 wherein said secure instrument connector comprises a plug fitting within said power hose/cord connector of said surgical instrument.

5. The cleaning tool of claim 1 wherein said secure instrument connector comprises a tubular portion having a bore therein, said power hose/cord connector of said surgical instrument being slideably positioned within said bore.

6. The cleaning tool of claim 1 wherein said handle has a radiused configuration and a smooth surface, said surface being free of corners, edges, protrusions, snags and catches whereby said handle is incapable of cutting, puncturing, catching or snagging rubber gloves worn by a person utilizing the tool.

7. The cleaning tool of claim 1 wherein said tool has a cross bar extending through said body on opposite sides thereof, said cross bar being adjacent said other end, whereby said cross bar may be held in the palm of one's hand with one's fingers wrapped around the cross bar and said body extending from said hand between said fingers.

8. The cleaning tool of claim 7 wherein said handle has an anvil at said other end, said cross bar extending on opposite sides of said anvil.

9. The cleaning tool of claim 1 wherein said tool body and handle are made of rugged, rigid material to withstand pounding on said handle, dropping the tool, a person stepping on the tool, all without misshaping the tool.

10. The cleaning tool of claim 1 wherein said body and handle are made of materials chosen from the group of materials consisting of metals and plastics.

11. The cleaning tool of claim 1 wherein said secure instrument connector has a diameter, said body between said secure instrument connector and said other end having a diameter less than said secure instrument connector diameter, said cross bar having a diameter less than said handle diameter.

12. The cleaning tool of claim 1 wherein said cross bar has a diameter less than one-half of said handle diameter.

13. The cleaning tool of claim 1 wherein said tool has an O-ring groove extending circumferentially around said secure instrument connector groove and extending radially thereof, an O-ring in said groove, said O-ring being compressed in said O-ring groove and between said hose connector and said tool when said tool is connected to said power hose/cord connector of said surgical instrument, the compression of said O-ring frictionally securing said tool and said surgical instrument together.

14. The cleaning tool of claim 13 further comprising a lock, said lock including a pair of diametrically opposed detents, and an L-shaped opening in which the detents are positioned, said detents being on one of said power hose/cord connector of said surgical instrument and said secure instrument connector, said L-shaped opening being on the other of said secure instrument connector and said power hose/cord connector of said surgical instrument, said detents being positioned in said L-shaped opening by moving said secure instrument connector and said power hose/cord connector both axially and rotatably of each other.

15. The cleaning tool of claim 14 wherein said O-ring holds said detents in said L-shaped opening whereby said secure instrument connector and said pneumatic hose connector are frictionally secured together.

16. A cleaning tool for powered surgical instruments having a conventional power hose/cord connector thereon comprising a tool body, said tool body having opposite ends and an axis extending between said ends, a secure instrument connector at one of said ends adapted to be secured to both sizes of said conventional power hose/cord connectors, a handle at the other of said ends, said handle allowing control of said tool body over axial movement and rotary movement and the accurate positioning of said instrument securely connected to said body single-handedly, said handle being spaced from said secure instrument connector, said secure instrument connector providing a hermetic seal between said tool body and said surgical instrument when secured to said surgical instrument whereby said surgical instrument may be cleaned, scoured and sterilized without damaging said instrument or unnecessarily exposing said instrument or said handle to the cleaning and sterilization agents used, said secure instrument connector being adapted to be securely fastened to said power hose/cord connector of said surgical instrument, said-power hose/cord connector and said secure instrument connector having sliding contiguous surfaces thereon providing said hermetic seal, and a lock, whereby said surgical instrument and said tool body may be connected and not be unintentionally disconnected once connected.

17. A cleaning tool for powered surgical instruments having a conventional power hose/cord connector thereon comprising a tool body, said tool body having opposite ends and an axis extending between said ends, a secure instrument connector at one of said ends adapted to be secured to both sizes of said conventional power hose/cord connectors, a handle at the other of said ends, said handle allowing control of said tool body over axial movement and rotary movement and the accurate positioning of said instrument securely connected to said body single-handedly, said handle being spaced from said secure instrument connector, said secure instrument connector providing a hermetic seal between said tool body and said surgical instrument when secured to said surgical instrument whereby said surgical instrument may be cleaned, scoured and sterilized without damaging said instrument or unnecessarily exposing said instrument or said handle to the cleaning and sterilization agents used, said secure instrument connector being adapted to be securely fastened to said power hose/cord connector of said surgical instrument, said power hose/cord connector and said secure instrument connector having sliding contiguous surfaces thereon providing said hermetic seal, and a lock, whereby said surgical instrument and said tool body may be connected and not be unintentionally disconnected once connected, said handle having a radiused configuration and a smooth surface, said surface being free of corners, edges, protrusions, snags and catches whereby said handle is incapable of cutting, puncturing, catching or snagging rubber gloves worn by a person utilizing the tool.

18. A cleaning tool for powered surgical instruments having a conventional power hose/cord connector thereon comprising a tool body, said tool body having opposite ends and an axis extending between said ends, a secure instrument connector at one of said ends adapted to be secured to both sizes of said conventional power hose/cord connectors, a handle at the other of said ends, said handle allowing control of said tool body over axial movement and rotary movement and the accurate positioning of said instrument securely connected to said body single-handedly, said handle being spaced from said secure instrument connector, said secure instrument connector providing a hermetic seal between said tool body and said surgical instrument when secured to said surgical instrument whereby said surgical instrument may be cleaned, scoured and sterilized without damaging said instrument or unnecessarily exposing said instrument or said handle to the cleaning and sterilization agents used, said secure instrument connector being adapted to be securely fastened to said power hose/cord connector of said surgical instrument, said power hose/cord connector and said secure instrument connector having sliding contiguous surfaces thereon providing said hermetic seal, and a lock, whereby said surgical instrument and said tool body may be connected and not be unintentionally disconnected once connected, said tool having a cross bar extending through said body on opposite sides thereof, said cross bar being adjacent said other end, whereby said cross bar may be held in the palm of one's hand with one's fingers wrapped around the cross bar and said body extending from said hand between said fingers.

19. A cleaning tool for powered surgical instruments having a conventional power hose/cord connector thereon comprising a tool body, said tool body having opposite ends and an axis extending between said ends, a secure instrument connector at one of said ends adapted to be secured to both sizes of said conventional power hose/cord connectors, a handle at the other of said ends, said handle allowing control of said tool body over axial movement and rotary movement and the accurate positioning of said instrument securely connected to said body single-handedly, said handle being spaced from said secure instrument connector, said secure instrument connector providing a hermetic seal between said tool body and said surgical instrument when secured to said surgical instrument whereby said surgical instrument may be cleaned, scoured and sterilized without damaging said instrument or unnecessarily exposing said instrument or said handle to the cleaning and sterilization agents used, said secure instrument connector being adapted to be securely fastened to said power hose/cord connector of said surgical instrument, said power hose/cord connector and said secure instrument connector having sliding contiguous surfaces thereon providing said hermetic seal, and a lock, whereby said surgical instrument and said tool body may be connected and not be unintentionally disconnected once connected, said tool having a cross bar extending through said body on opposite sides thereof, said cross bar being adjacent said other end, whereby said cross bar may be held in the palm of one's hand with one's fingers wrapped around the cross bar and said body extending from said hand between said fingers, said secure instrument connector having a diameter, said body between said secure instrument connector and said other end having a diameter less than said secure instrument connector diameter, said cross bar having a diameter less than said handle diameter.

20. A cleaning tool for powered surgical instruments having a conventional power hose/cord connector thereon comprising a tool body, said tool body having opposite ends and an axis extending between said ends, a secure instrument connector at one of said ends adapted to be secured to both sizes of said conventional power hose/cord connectors, a handle at the other of said ends, said handle allowing control of said tool body over axial movement and rotary movement and the accurate positioning of said instrument securely connected to said body single-handedly, said handle being spaced from said secure instrument connector, said secure instrument connector providing a hermetic seal between said tool body and said surgical instrument when secured to said surgical instrument whereby said surgical instrument may be cleaned, scoured and sterilized without damaging said instrument or unnecessarily exposing said instrument or said handle to the cleaning and sterilization agents used, said secure instrument connector being adapted to be securely fastened to said power hose/cord connector of said surgical instrument, said power hose/cord connector and said secure instrument connector having sliding contiguous surfaces thereon providing said hermetic seal, and a lock, whereby said surgical instrument and said tool body may be connected and not be unintentionally disconnected once connected, said secure instrument connector having a diameter, said body between said secure instrument connector and said other end having a diameter less than said secure instrument connector diameter.

21. A cleaning tool for powered surgical instruments having a conventional power hose/cord connector thereon comprising a tool body, said tool body having opposite ends and an axis extending between said ends, a secure instrument connector at one of said ends adapted to be secured to both sizes of said conventional power hose/cord connectors, a handle at the other of said ends, said handle allowing control of said tool body over axial movement and rotary movement and the accurate positioning of said instrument securely connected to said body single-handedly, said handle being spaced from said secure instrument connector, said secure instrument connector providing a hermetic seal between said tool body and said surgical instrument when secured to said surgical instrument whereby said surgical instrument may be cleaned, scoured and sterilized without damaging said instrument or unnecessarily exposing said instrument or said handle to the cleaning and sterilization agents used, said secure instrument connector being adapted to be securely fastened to said power hose/cord connector of said surgical instrument, said power hose/cord connector and said secure instrument connector having sliding contiguous surfaces thereon providing said hermetic seal, and a lock, whereby said surgical instrument and said tool body may be connected and not be unintentionally disconnected once connected, said tool having a cross bar extending through said body on opposite sides thereof, said cross bar being adjacent said other end, whereby said cross bar may be held in the palm of one's hand with one's fingers wrapped around the cross bar and said body extending from said hand between said fingers, said secure instrument connector having a diameter, said body between said secure instrument connector and said other end having a diameter less than said secure instrument connector diameter, said cross bar having a diameter less than said handle diameter, said cross bar has a diameter less than one-half of the diameter of said handle diameter, said handle having a radiused configuration and a smooth surface, said surface being free of corners, edges, protrusions, snags and catches whereby said handle is incapable of cutting, puncturing, catching or snagging rubber gloves worn by a person utilizing the tool.

22. A cleaning tool for powered surgical instruments having a conventional power hose/cord connector thereon comprising a tool body, said tool body having opposite ends and an axis extending between said ends, a secure instrument connector at one of said ends adapted to be secured to said conventional power hose/cord connector, a handle at the other of said ends, said handle having a finger grasping portion, a central locator for positioning two fingers on both sides of said locator and on said finger grasping portion, and a central portion which may be pulled by the fingers comfortably into the palm of the hand thereby allowing the person grasping the handle to have positive control over the positioning and the axial and rotary movement of the tool during the cleaning process and to have the "physical feel" in both fingers and the palm confirming said control over a surgical instrument during the cleaning process without touching the tool.

23. A cleaning tool for powered surgical instruments having a conventional power hose/cord connector thereon comprising a tool body, said tool body having opposite ends and an axis extending between said ends, a secure instrument connector at one of said ends adapted to be secured to said conventional power hose/cord connector, a handle at the other of said ends, said handle having a finger grasping portion, a central locator for positioning two fingers on both sides of said locator and on said finger grasping portion, and a central portion which may be pulled by the fingers comfortably into the palm of the hand thereby allowing the person grasping the handle to have positive control over the positioning and the axial and rotary movement of the tool during the cleaning process, thereby-the surgical instrument may be cleaned, scoured and disinfected without damage to the surgical instrument or unnecessarily exposing the handle or the instrument to the cleaning and disinfectant agents utilized or unintentional separation of the tool from the instrument or dropping of the instrument.

\* \* \* \* \*